(12) United States Patent
Matsunobu

(10) Patent No.: US 10,820,793 B2
(45) Date of Patent: Nov. 3, 2020

(54) BIOLOGICAL OBJECT OBSERVATION SYSTEM AND NON-TRANSITORY COMPUTER-READABLE MEDIUM

(71) Applicant: NIDEK CO., LTD., Gamagori-shi, Aichi (JP)

(72) Inventor: Go Matsunobu, Okazaki (JP)

(73) Assignee: NIDEK CO., LTD., Gamagori-shi (JP)

( * ) Notice: Subject to any disclaimer, the term of this patent is extended or adjusted under 35 U.S.C. 154(b) by 232 days.

(21) Appl. No.: 15/946,829

(22) Filed: Apr. 6, 2018

(65) Prior Publication Data

US 2018/0289254 A1 Oct. 11, 2018

(30) Foreign Application Priority Data

Apr. 6, 2017 (JP) ................. 2017-076174

(51) Int. Cl.
*A61B 3/00* (2006.01)
*A61B 3/14* (2006.01)
(Continued)

(52) U.S. Cl.
CPC .......... *A61B 3/0041* (2013.01); *A61B 3/0075* (2013.01); *A61B 3/102* (2013.01); *A61B 3/13* (2013.01); *A61B 3/14* (2013.01)

(58) Field of Classification Search
CPC ......... A61B 3/14; A61B 3/102; A61B 3/0025; A61B 3/12; A61B 3/1025; A61B 3/0008; A61B 3/1005; A61B 3/113; A61B 3/1225; A61B 3/0058; A61B 3/107; A61B 3/117; A61B 3/13; A61B 3/1015; A61B 3/145; A61B 3/10; A61B 3/0041; A61B 3/152; A61B 3/103; A61B 3/0033; A61B 3/0075; A61B 3/0091; A61B 3/112; A61B 3/18; A61B 5/0066; A61B 2576/02; A61B 3/005; A61B 3/101; A61B 3/1208; A61B 3/1241; A61B 3/125; A61B 3/158; A61B 5/0013; A61B 2560/0475; A61B 3/00; A61B 3/0083; A61B 3/028; A61B 3/032; A61B 3/11; A61B 3/111; A61B 3/1233; A61B 3/132; A61B 5/0075; A61B 5/163;
(Continued)

(56) References Cited

U.S. PATENT DOCUMENTS

2018/0035887 A1* 2/2018 Nakanishi ............... A61F 9/007

FOREIGN PATENT DOCUMENTS

JP 2015-163092 A 9/2015

* cited by examiner

*Primary Examiner* — Collin X Beatty
*Assistant Examiner* — Grant A Gagnon
(74) *Attorney, Agent, or Firm* — Oliff PLC

(57) ABSTRACT

A biological object observation system includes an observation optical unit, a photodetector, a display unit, a detection unit, and a processor. The observation optical unit includes an optical system that guides a luminous flux from a biological object and a drive unit that drives the optical system. The photodetector receives optical information in accordance with the biological object. The display unit displays an observation image of the biological object generated on the basis of the optical information. The detection unit detects one of a position and a movement of an object in a display region of the displayed observation image. The processor controls the drive unit in accordance with the one of the position and the movement of the object that is detected.

9 Claims, 10 Drawing Sheets

(51) Int. Cl.
*A61B 3/10* (2006.01)
*A61B 3/13* (2006.01)

(58) Field of Classification Search
CPC .......... A61B 5/489; A61B 2017/00716; A61B 2503/10; A61B 2503/20; A61B 2560/0223; A61B 2560/0228; A61B 2560/0233; A61B 2560/0266; A61B 2560/0271; A61B 3/0016; A61B 3/024; A61B 3/063; A61B 3/08; A61B 3/1035; A61B 3/1173; A61B 3/1176; A61B 3/1216; A61B 3/135; A61B 3/15; A61B 3/154; A61B 3/156; A61B 5/0022; A61B 5/0059; A61B 5/02416; A61B 5/0261; A61B 5/1075; A61B 5/1079; A61B 5/1103; A61B 5/1114; A61B 5/1116; A61B 5/1124; A61B 5/1128; A61B 5/1176; A61B 5/1455; A61B 5/165; A61B 5/18; A61B 5/4821; A61B 5/4848; A61B 5/486; A61B 5/6803; A61B 5/7275; A61B 5/7425; A61B 8/10; A61B 90/20
USPC ........................................................ 351/206
See application file for complete search history.

BIOLOGICAL OBJECT OBSERVATION SYSTEM AND NON-TRANSITORY COMPUTER-READABLE MEDIUM

CROSS REFERENCE TO RELATED APPLICATION

This application is based upon and claims the benefit of priority of Japanese Patent Application No. 2017-076174 filed on Apr. 6, 2017, the contents of which are incorporated herein by reference in its entirety.

BACKGROUND

The present disclosure relates to a biological object observation system and a non-transitory computer-readable medium that are used to observe a biological object.

Various systems are known that allows a user (such as a surgeon) to observe a biological object when an operation, an examination, a diagnosis, or the like is performed. For example, in a known ophthalmic surgical microscope, an observation optical system includes an observation optical path for the user's right eye and an observation optical path for the user's left eye. By using both eyes to observe a patient's eye, which is an object to be observed, through left and right eyepieces, the user stereoscopically views the patient's eye. Further, a technology (optical coherence tomography (OCT)) is known that generates a tomographic image of a biological object and allows the user to observe the tomographic image. In OCT, a measuring beam is scanned on the biological object, and a tomographic image of the scanned position is generated (captured). Further, in the field of ophthalmology, for example, various biological object observation systems are used, such as an eye fundus camera, a scanning laser ophthalmoscope (SLO), or the like.

SUMMARY

In the biological object observation system, in order to allow the user to more appropriately observe the biological object, an observation state (an optical system of the system or a display method of the captured image, for example) is adjusted as necessary. For example, in the surgical microscope, when a position that the user is paying attention to is frequently changed, or the like, it is preferable that the focus of the position to which attention is paid is rapidly and finely brought into focus. Further, in the OCT, it is preferable that an image capture position of the tomographic image, a display method of the captured image, and the like are changed rapidly and accurately as the user desires. However, in a known general biological object observation system, when the user adjusts the observation state to an optimal state, it is necessary to finely operate an operating button or the like, and this may obstruct the progress of an operation, an examination, or the like.

Embodiments of the broad principles derived herein provide a biological object observation system and a non-transitory computer-readable medium storing computer-readable instructions that allow a user to easily input a command to adjust an observation state.

Embodiments provide a biological object observation system that includes an observation optical unit including an optical system that guides a luminous flux from a biological object that is an object to be observed and a drive unit that drives the optical system, a photodetector receiving optical information in accordance with the biological object, a display unit displaying an observation image of the biological object generated on the basis of the optical information received by the photodetector, a detection unit detecting one of a position and a movement of an object in a display region of the observation image displayed by the display unit, and a processor controlling an operation of the biological object observation system, and the processor controls the drive unit of the observation optical unit in accordance with the one of the position and the movement of the object, in the display region of the observation image, detected by the detection unit.

Embodiments further provide a non-transitory computer-readable medium storing computer-readable instructions that, when executed by a processor of a biological object observation system, cause the biological object observation system to perform a process, the biological object observation system including an observation optical unit including an optical system that guides a luminous flux from a biological object and a drive unit that drives the optical system, a photodetector receiving optical information in accordance with the biological object, a display unit displaying an observation image of the biological object generated on the basis of the optical information received by the photodetector, and a detection unit detecting one of a position and a movement of an object in a display region of the observation image displayed by the display unit, and the process including controlling the drive unit of the observation optical unit in accordance with the one of the position and the movement of the object, in the display region of the observation image, detected by the detection unit.

DETAILED DESCRIPTION

Overview

Figure 1:
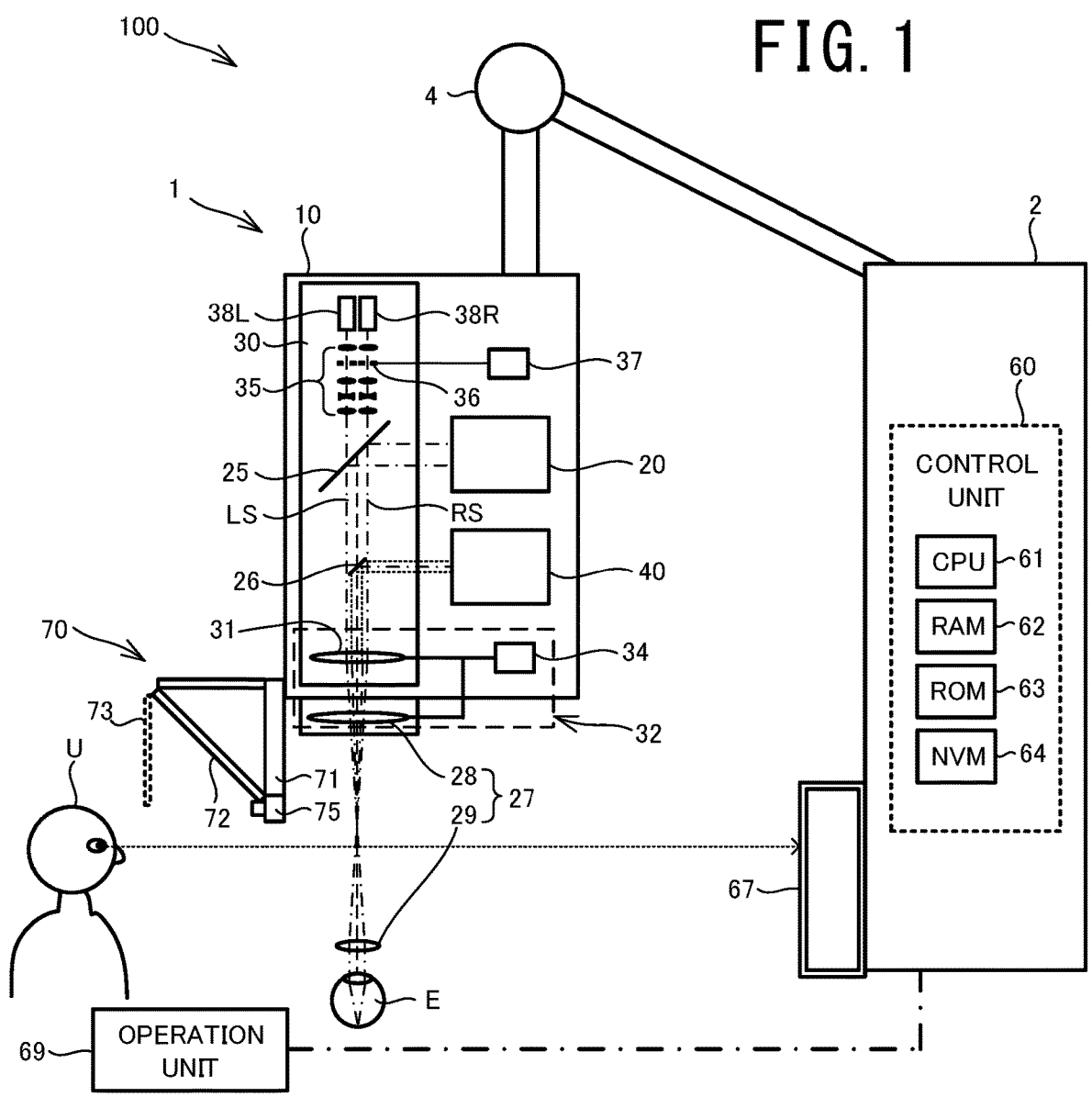
FIG. 1 is a view illustrating a general configuration of a biological object observation system 100.

A biological object observation system exemplified in the present disclosure includes an observation optical unit, a photodetector, a display unit, a detection unit, and a processor. The observation optical unit includes an optical system that guides a luminous flux from a biological object and a drive unit that drives the optical system. The photodetector receives optical information in accordance with the biological object. The display unit displays an observation image of the biological object generated on the basis of the optical information received by the photodetector. The detection unit detects a position of an object in a display region of the observation image displayed by the display unit. The processor controls the drive unit of the observation optical unit in accordance with the one of the position and the movement of the object, in the display region of the observation image, that is detected.

In this case, the processor can use position information or movement information of an object detected in the display region of the observation image and control the drive unit of the observation optical unit. Thus, the user can input an appropriate command simply by adjusting a position or a movement of the user's finger on the display region of the observation image, in contrast to a case in which the user operates a plurality of operating buttons, a case in which the user finely adjusts the number of times that an operating button is operated, or the like.

The display unit may be an aerial display that includes a monitor and an imaging unit. The imaging unit may cause an aerial image, which is an actual image, to be displayed in space by causing light beams emitted from a display surface of the monitor to form an image. The detection unit may detect one of a position and a movement of an object in a region in space in which the aerial image is displayed. In this case, the user can input the position information or the operation information into the biological object observation system, without touching an object. As a result, the user can adjust the observation state in an appropriate state while maintaining the cleanliness of the user's hand and the like.

However, the display unit may be a normal monitor that displays an image on a display screen. Further, the detection unit may be a touch panel that detects a position or a movement of an object touching the display screen of the monitor. In this case also, the user can input an appropriate command simply by adjusting the position or the movement of the user's finger or the like.

The observation optical unit may include a microscope unit that includes a microscope optical system and a microscope focus adjustment drive unit. The microscope optical system may guide an observation luminous flux allowing a user to observe the magnified biological object. The microscope focus adjustment drive unit may be provided on a light path of the observation luminous flux in the microscope optical system, and may adjust a focus of the microscope optical system. The photodetector may capture the observation image by receiving the observation luminous flux guided by the microscope optical system. The processor may set a target region on the observation image captured by the photodetector, on the basis of the one of the position and the movement of the object, in the display region of the observation image, detected by the detection unit. The processor may acquire a focus state of the microscope optical system, and may adjust a focus of the target region in the observation image by driving the microscope focus adjustment drive unit on the basis of an acquisition result of the focus state of the microscope optical system. In this case, the focus of the position to which attention is to be paid can be appropriately adjusted by the user simply moving the user's finger or the like on the position, on the observation image, to which the user desires to pay particular attention.

A specific method for setting a target region on the basis of the position or the movement of the object detected by the detection unit may be set as appropriate. For example, when the position of the detected object is detected as a point, the processor may set, as the target region, a region that includes the position of the detected point (a region centering on the detected point and the like, for example). In this case, the size of the target region may be set in advance, or may be set in accordance with a command from the user. Further, when the position or the movement of the detected object forms a line, the processor may set, as the target region, a region that includes the line. Further, when the position or the movement of the detected object forms a surface, the processor may set the formed surface as the target region.

The processor may receive an input of an offset amount (deviation amount) of a position that the user desires to bring into focus, with respect to a focus position of a microscope focus adjusted on the basis of an acquisition result of a microscope focus state. The processor may focus the microscope focus on a position that deviates by the input offset amount from the focus position that is based on the acquisition result of the microscope focus state. In this case, the focus may be focused on the position that deviates by the desired amount from a normal focus position that is focused by automatic focusing. As a result, the user can more appropriately observe the biological object.

The observation optical unit may include an OCT unit that includes an OCT light source, a light splitter, a scanning drive unit, and an OCT photodetector. The OCT light source may emit OCT light. The light splitter may split a luminous flux emitted from the OCT light source into a measurement luminous flux and a reference luminous flux. The scanning drive unit may cause the measurement luminous flux split by the light splitter to scan on the biological object. The OCT photodetector may receive interference light obtained by synthesis of the reference luminous flux and the measurement luminous flux reflected by the biological object. The processor may control the scanning drive unit of the OCT unit, in accordance with the one of the position and the movement of the object detected, in the display region of the observation image, by the detection unit. In this case, simply by the user moving the user's finger or the like on a position, on the observation image, to which the user desires to pay attention, an OCT signal of the position to which attention is to be paid can be appropriately acquired. The OCT signal may be, for example, an OCT signal for acquiring a two-dimensional tomographic image, a three-dimensional tomographic image, a motion contrast image, or the like.

A specific method for controlling a scanning position of the measurement luminous flux on the basis of the position or the movement of the object detected by the detection unit may be set as appropriate. For example, when the position of the detected object is detected as a point, the processor may cause the scanning of the measurement luminous flux on the basis of the position of the detected point (to scan on a scanning line that traverses the detected point, for example). Further, when the position or the movement of the detected object forms a line, the processor may cause the scanning of the measurement luminous flux on the basis of the position of the detected line (on at least one of a scanning line that overlaps the detected line and a scanning line that intersects the detected line, for example). Further, when the position or the movement of the detected object forms a surface, the process may cause the scanning of the measurement luminous flux on the basis of the position of the formed surface (such that a three-dimensional tomographic image or a motion contrast image is acquired in the formed surface, for example).

The observation optical unit may include the microscope unit and the OCT unit. The OCT unit may include an OCT light adjustment drive unit. The OCT light adjustment drive unit may be provided on at least one of an optical path of the measurement luminous flux and an optical path of the reference luminous flux. The OCT light adjustment drive unit may adjust at least one of an optical path length difference between the measurement luminous flux and the reference luminous flux and a focus of an optical system that guides the measurement luminous flux. The processor may control the scanning drive unit of the OCT unit in accordance with the one of the position and the movement of the object, in the display region of the observation image, detected by the detection unit. Further, the processor may drive the OCT light adjustment drive unit in accordance with a change in the focus state of the microscope optical system.

In this case, simply by the user moving the user's finger or the like on a position, on the observation image, to which the user desires to pay attention, as well as the focus of the position to which attention is to be paid being appropriately adjusted, of a range observed using the microscope unit, the OCT signal of the position to which attention is to be paid can be appropriately acquired. Furthermore, in addition to the focus of the target region being observed using the microscope unit being appropriately adjusted, at least one of the optical path length difference and the focus (hereinafter referred to as an "OCT focus") of the OCT unit can be appropriately adjusted. More specifically, when only performing adjustment of an automatic optical path length (OPL) that searches for a position at which the tomographic image is acquired while changing the optical path length difference, it may be necessary for the processor to search a wide area while causing significant variations in the optical path length difference. Similarly, when the OCT focus and the focus of the microscope unit (hereinafter referred to as the "microscope focus") are independently adjusted, the adjustment of the OCT focus may take time. In contrast to this, the processor can adjust the OCT light in concert with the adjustment of the microscope focus. As a result, the adjustment of the OCT light can be rapidly and appropriately performed.

When the optical path length difference is adjusted, the OCT light adjustment drive unit may be provided with an optical path length difference adjustment drive unit that adjusts an optical path length difference of the measurement luminous flux and the reference light flux. When the OCT focus is adjusted, the OCT light adjustment drive unit may be provided with an OCT focus adjustment drive unit that is provided on the optical path of the measurement luminous flux and that adjusts the focus of an optical system that guides the measurement luminous flux.

A specific method for driving the optical path length difference adjustment drive unit in accordance with the change of the microscope focus state in the target region may be selected as appropriate. For example, on the basis of a drive amount of the microscope focus adjustment drive unit, the processor may calculate a change amount ΔZ of the position being observed, and may determine a drive amount of the optical path length difference adjustment drive unit from the calculated ΔZ. Further, the processor may use a ratio between a movement amount of the microscope focus corresponding to the drive amount of the microscope focus adjustment drive unit and a fluctuation amount of the optical path length difference corresponding to the drive amount of the optical path length difference adjustment drive unit. In this case, the processor may determine the drive amount of the optical path length difference adjustment drive unit in accordance with the drive amount of the microscope focus adjustment drive unit and the above-described ratio. Further, the processor may detect a deviation of a current microscope focus with respect to an appropriate microscope focus, and may determine the drive amount of the optical path length difference adjustment drive unit on the basis of the detected microscope focus deviation. In this case also, the optical path length difference can be appropriately adjusted in accordance with the change in the microscope focus state. The processor may drive the optical path length difference adjustment drive unit after driving the microscope focus adjustment drive unit, or may drive the microscope focus adjustment drive unit and the optical path length difference adjustment drive unit simultaneously in concert with each other.

The processor may analyze the OCT signal acquired via the OCT photodetector and may drive the optical path length difference adjustment drive unit on the basis of the change of the microscope focus state in the target region and an analysis result of the OCT signal. In this case, the optical path length difference adjustment drive unit can be driven while also taking into account the analysis result of the actually acquired OCT signal. Thus, the adjustment of the optical path length difference can be more appropriately performed.

In this case, a specific method for controlling the optical path length difference adjustment drive unit may be selected as appropriate. For example, the processor may drive the optical path length difference adjustment drive unit on the basis of the analysis result of the OCT signal (to a position at which a level of the OCT signal is equal to or greater than a threshold value, for example), after driving the optical path length difference adjustment drive unit on the basis of the drive amount of the microscope focus adjustment drive unit. Further, the processor may determine a timing to stop the driving, by referring to the analysis result of the OCT signal while driving the optical path length difference adjustment drive unit on the basis of the drive amount of the microscope focus adjustment drive unit. In addition, the optical path length difference adjustment drive unit may be driven without using the analysis result of the OCT signal.

Further, the processor may drive the OCT focus adjustment drive unit on the basis of the change of the microscope focus state in the target region and the analysis result of the OCT signal. In this case, the OCT focus adjustment drive unit can be driven while also taking into account the analysis result of the actually acquired OCT signal. Thus, the adjustment of the OCT focus can be more appropriately performed. A specific method for controlling the OCT focus adjustment drive unit may be selected as appropriate, similarly to the specific control method of the optical path length difference adjustment drive unit.

The biological object observation system may be a single device in which the microscope unit and the OCT unit are combined. The biological object observation system may be a system that includes the microscope unit and the OCT unit that is a device separate from the microscope unit. Further, the processor that controls the adjustment of the OCT light may be a processor provided in the OCT unit, or may be a processor provided in the microscope unit. A processor of a personal computer or the like connected to each of the microscope unit and the OCT unit may control the adjustment of the OCT light. Processors provided in a plurality of devices (such as the microscope unit and the OCT device) may work in concert to control the adjustment of the OCT light.

Further, each of the scanning position and the target region may be independent of each other, without setting the scanning position of the OCT light in the target region. The adjustment of the OCT light need not necessarily be linked to the change in the microscope focus in the target region.

The processor may acquire the microscope focus state on the basis of a signal in the set target region, among signals from the photodetector. In this case, the processor can use the photodetector for acquiring the observation image and appropriately acquire the microscope focus state for focusing the target region. Thus, the biological object observation system can appropriately acquire the microscope focus state while suppressing an increase in a dedicated configuration for acquiring the microscope focus state.

As a method for acquiring the microscope focus state on the basis of the signal from the photodetector, various methods may be applied. For example, the processor may acquire the microscope focus state using a contrast detection method. In this case, the processor may acquire the microscope focus state by analyzing the image in the target region in the observation image captured by the photodetector while changing the microscope focus, and causing a position at which the contrast of the image in the target region is high to be the position at which the microscope focus is in focus.

However, a method other than the contrast detection method may be used. For example, the processor may acquire the microscope focus state using an image surface phase difference detection method. In this case, phase difference pixels, which are formed in a non-symmetrical shape in the left-right direction, may be embedded among at least one of the pixels of the photodetector in order to detect a phase difference (parallax) of the image. The processor may calculate the phase difference on the basis of a signal obtained by light injected from one of the left and right directions being selectively received by the phase difference pixel. The processor may acquire the focus state by causing a position at which the phase difference is smaller to be the position at which the microscope focus is in focus.

Further, a phase difference detection method may be applied that uses a phase difference detection sensor separate from the photodetector. In this case, for example, a separator lens that creates two images from the observation luminous flux, and a phase difference detection sensor for detecting the phase difference (the parallax) from the two images may be provided. The processor may calculate the phase difference on the basis of a signal obtained using the phase difference detection sensor, and may acquire the microscope focus state by causing the position at which the phase difference is smaller to be the position at which the microscope focus is in focus.

Further, for example, the microscope focus state may be acquired using an astigmatism detection method, a knife edge method, the Foucault method, a critical angle method, or the like. The astigmatism detection method is a method that detects the focus state using an astigmatism that occurs due to a difference between focal positions of a cylindrical lens and an objective lens. The knife edge method is a method in which a wall (knife edge) that blocks light on one surface of an optical path is provided on an objective lens focal point between an objective lens and a two-way photodiode, and the focus state is detected by using an amount of light injected into the two-way photodiode. The Foucault method is a method that detects the focus state by detecting a change in the optical path occurring due to a relationship between a position of a focal point of an objective lens and a position of a prism surface, using two two-way photodiodes. The critical angle method is a method that detects the focus state by detecting, using a two-way photodiode, a change in a ratio of reflected light and transmitted light, using a critical angle prism.

A hybrid method may be used in which a plurality of detection methods are used in combination. For example, a hybrid detection method may be adopted, such as a combination of the contrast detection method and the image surface phase difference detection method. When the hybrid detection method is used, even if an error occurs using one of the detection methods, the focus state can be appropriately detected by another detection method.

The processor may detect a movement of a subject captured in the observation image by performing image processing on the captured observation image. The subject may be a biological object, a position of an opening of a front lens arranged at a fixed position with respect to the biological object, or the like, for example. The processor may cause a position of the target region in the observation image to follow (track) in accordance with the detected movement of the subject. In this case, even if the subject moves, the good quality of the image of the target region can be maintained.

The observation optical unit may include an adjustable aperture and an aperture drive unit. The adjustable aperture may be provided on an optical path of the observation luminous flux in the microscope optical system, and may adjust a luminous flux diameter of the observation luminous flux. The aperture drive unit may drive the adjustable aperture. The processor may control the aperture drive unit in accordance with the one of the position and the movement of the object, in the display region of the observation image, detected by the detection unit. When the adjustable aperture is made smaller, the resolving power decreases, but as the focal depth becomes deeper, the focus can be more easily aligned. In contrast, when the adjustable aperture is made larger, the brightness of the range being observed becomes brighter, the resolving power is higher, and the focal depth can be shallower. The user can easily perform the adjustment by the adjustable aperture, simply by moving the user's finger or the like in the display region of the observation image.

The biological object observation system may be provided with the microscope unit only and not be provided with the OCT unit, or may be provided with the OCT unit and not be provided with the microscope unit. Further, at least part of the technology exemplified in the present disclosure may be applied to a configuration and control other than the microscope unit and the OCT unit. For example, in the field of ophthalmology, the adjustment of an image capture position, focus, or the like of an eye fundus camera, a scanning laser ophthalmoscope (SLO), or the like may be performed in accordance with one of the position and the movement of the object, in the display region of the observation image, detected by the detection unit.

The processor may control a display state or the like of the captured image (an orientation of the image, for example) in accordance with one of the position and the movement of the object, in the display region of the observation image, detected by the detection unit. In other words, the processor may control the observation state of the biological object in the biological object observation system in accordance with the position or the movement of the object, in the display region of the observation image, detected by the detection unit. In this case also, the user can easily input a command to adjust the observation state.

When an aerial display is used as a display unit at an actual medical site, there may be other effective methods of use of the aerial display other than the usage method described above. For example, when a medical operation or the like is being performed, there may be a case in which a surgeon or the like needs to share information that is not desired to be disclosed to the patient between a plurality of surgeons, nurses, and the like. In this type of case, conventionally, the only way to do this may be to communicate using a code word or the like. It is thus complicated to share, with a plurality of surgeons and nurses, the information that is not desired to be disclosed to the patient.

Here, the biological object observation system may be provided with an aerial display and a patient detection unit. The aerial display may include an imaging unit that causes an aerial image to be displayed in space, by causing light beams emitted from a display surface of a monitor to form an image. The patient detection unit may detect whether a patient is present on a treatment table on which the patient is placed. The processor may cause specific information (information that is not desired to be disclosed to the patient, for example) to be displayed in the aerial display when it is detected by the patient detection unit that the patient has been placed on the treatment table. Further, the processor may stop the display of the specific information in the aerial display when it is detected by the patient detection unit that the patient has moved away from the treatment table. In this case, in a state in which it is difficult to visually check display content in the aerial display when the patient is present on the treatment table, the specific information can be automatically displayed in the aerial display. Thus, work can be easily carried out while the specific information is displayed.

Embodiments

Hereinafter, an exemplary embodiment of the present disclosure will be described with reference to the drawings. The present embodiment illustrates a biological object observation system (hereinafter simply referred to as an "observation system") 100 for performing stereoscopic viewing and the like of a patient's eye during ophthalmic surgery. However, at least a portion of the technology illustrated in the present embodiment may also be applied to an observation system used for a purpose other than ophthalmology. Further, in the present embodiment, the observation system 100 is illustrated in which an observation image captured by a microscope unit 1 is stereoscopically displayed on a display 67. However, at least a portion of the technology illustrated in the present embodiment may be applied to an observation system that allows a user to observe a biological object using another method.

As illustrated in FIG. 1, the observation system 100 of the present embodiment includes the microscope unit 1, an OCT unit 40, and a control unit 60. Each of the microscope unit 1 and the OCT unit 40 is a type of an observation optical unit that includes an optical system and a drive unit to allow the user to observe the biological object. In the following description, a direction parallel to observation luminous fluxes RS and LS of the surgical microscope 1 is referred to as a Z direction, and a direction that intersects the Z direction is referred to as an XY direction.

The microscope unit 1 will be explained. As shown in FIG. 1, the microscope unit 1 of the embodiment includes a base unit 2, an arm unit 4, and an observation device 10. The base unit 2 is a portion that serves as the base of the microscope unit 1. In this embodiment, a control unit 60, which is described below, is built in the base unit 2. The arm unit 4 has at least one joint, and movably supports the observation device 10.

The observation device 10 includes an illumination optical system 20, a beam splitter 25, a reflection mirror 26, and an observation optical system (microscope optical system) 30. The illumination optical system 20 emits illumination light that illuminates a biological object (a patient's eye E in this embodiment) that is an observation object. The illumination optical system 20 is capable of emitting illumination light coaxial with the optical axis of the observation luminous flux RS for the right eye in the observation optical system 30 and illumination light coaxial with the optical axis of the observation luminous flux LS for the left eye in the observation optical system 30. However, the illumination light may be illumination light irradiated toward the observation object from an angle that differs from the optical axis of the observation luminous fluxes RS and LS. The observation luminous fluxes RS and LS in this embodiment refer to luminous fluxes guided by the observation optical system 30 to produce light to be observed by a user U, of the luminous fluxes from the observation object (the luminous fluxes of the illumination light reflected by the observation object, for example).

The beam splitter 25 is one example of an optical axis coupling element that makes the optical axis of the illumination light emitted by the illumination optical system 20 and the optical axes of the observation luminous fluxes RS and LS in the observation optical system 30 coaxial. The beam splitter 25 illustrated in FIG. 1 makes the optical axis of the illumination light and the optical axes of the observation luminous fluxes RS and LS coaxial by reflecting at least a portion of the illumination light emitted from the illumination optical system 20 and transmitting at least a portion of the observation luminous fluxes RS and LS from the observation object. The illumination light reflected by the beam splitter 25 travels along the same optical path as part of the optical path of the observation luminous fluxes RS and LS, in a direction opposite to the direction in which the observation luminous fluxes RS and LS travel, and is irradiated on the observation object.

The reflection mirror 26 reflects a measurement luminous flux for measuring an OCT signal emitted by the OCT unit 40 (to be described in detail below) toward the biological object. The reflection mirror 26 illustrated in FIG. 1 is provided in a position in which there is no interference with the observation luminous fluxes RS and LS and with illumination light (in the present embodiment, a position between the two observation luminous fluxes RS and LS). In FIG. 1, the reflection mirror 26 is provided between the beam splitter 25 and a microscope focus adjustment unit 32 (to be described below). However, the position of the reflection mirror 26 may be changed in accordance with a position of the OCT unit 40 or the like.

The observation optical system 30 guides the observation luminous flux from the observation object to allow the user to observe (stereoscopically view, in this embodiment) the observation object. The microscope unit 1 in this embodiment allows the user to stereoscopically view the observation object by causing a display (a stereoscopic image display in this embodiment) 67 to display an observation image to be observed with the right eye of the user U and an observation image to be observed with the left eye of the user U (that is, by causing the display 67 to display left and right microscopic images). The microscope unit 1 can thus allow the user U to stereoscopically view the observation object. Therefore, the observation optical system 30 guides the right eye observation luminous flux RS from the observation object to a right eye photodetector 38R, and guides the left eye observation luminous flux LS from the observation object to a left eye photodetector 38L. The control unit 60 controls the image display of the display 67 on the basis of signals from the two photodetectors 38R and 38L. Any of various kinds of displays, such as a three-dimensional display, a stereo viewer, and a head mounted display, for example, may be used for the display to cause stereoscopic vision of the observation object. There is no need to separately provide the right eye photodetector 38R, to which the right eye observation luminous flux RS is guided, and the left eye photodetector 38L, to which the left eye observation luminous flux LS is guided. For example, an area to which the right eye observation luminous flux RS is guided and an area to which the left eye observation luminous flux LS is guided may be provided in an imaging area of a single photodetector.

The user may observe the biological object when a wide angle observation unit 27 is used. The wide angle observation unit 27 is used to widen an observation angle of view of the ocular fundus of the patient's eye E. For example, the user may use the wide angle observation unit 27 when observing the ocular fundus of the patient's eye E. When observing the anterior ocular segment of the patient's eye E, the user may remove the wide angle observation unit 27. In this way, the user can perform an appropriate observation in accordance with each portion. The wide angle observation unit 27 of the present embodiment includes a reducing lens 28, which is arranged on the observation optical system 30 side, and a front lens 29, which is arranged on the patient's eye E side.

The observation optical system 30 includes an objective lens 31, the microscope focus adjustment unit 32, a zoom/aperture optical system 35, and the photodetectors 38R and 38L described above. The microscope focus adjustment unit 32 is provided on optical paths of the observation luminous fluxes RS and LS. The microscope focus adjustment unit 32 can adjust the focus (the microscope focus) of the observation optical system 30. The zoom/aperture optical system 35 can change an image capture magnification of an image of the biological object captured by the photodetectors 38R and 38L, and can adjust a flux diameter of the observation luminous flux. More specifically, in the present embodiment, the image capture magnification is changed by at least one of the lenses in the zoom/aperture optical system 35 being moved in the direction that is along the observation luminous fluxes RS and LS. Further, an adjustable aperture 36 is provided on each of the optical paths of the left and right observation luminous fluxes, in the zoom/aperture optical system 35. An opening diameter of the adjustable aperture 36 is adjusted by an aperture drive unit (a motor or the like) 37, and the flux diameter of the observation luminous flux is thus adjusted.

As an example, the microscope focus adjustment unit 32 of the present embodiment includes the objective lens 31 and a microscope focus adjustment drive motor 34. Further, when the wide angle observation unit 27 is used, the reducing lens (positive lens) 28 of the wide angle observation unit 27 is also included in the microscope focus adjustment unit 32. The microscope focus adjustment drive motor 34 moves the objective lens 31 (the objective lens 31 and the reducing lens 28 when the wide angle observation unit 27 is used) in a direction that is along the observation luminous fluxes RS and LS. As a result, the focus of the observation optical system 30 of the microscope unit 1 (hereinafter referred to as an "microscope focus") is changed. In the present embodiment, as the microscope focus adjustment drive motor 34, a motor that moves the objective lens 31 and a motor that moves the reducing lens 28 are separately provided. Thus, both the objective lens 31 and the reducing lens 28, which is arranged on the outside of a lens barrel of the objective lens 31, are appropriately moved. However, the objective lens 31 and the reducing lens 28 may be moved by a single motor.

The configuration of the microscope focus adjustment unit may be changed. For example, the microscope focus adjustment unit may adjust the microscope focus by moving at least one of the lenses in the zoom/aperture optical system 35 in a direction that is along the observation luminous fluxes RS and LS. In this case, in the example shown in FIG. 1, for example, the lens to be moved in the zoom/aperture optical system 35 is, of the lenses arranged in order of a positive lens, a negative lens, a positive lens, and a positive lens from an upstream side on the optical path, the positive lens on the most upstream side. Further, the microscope focus adjustment unit may include a negative lens that is located further to the photodetectors 38R and 38L side on the optical path than the objective lens 31. In this case, the microscope focus adjustment unit may adjust the microscope focus by using the microscope focus adjustment drive motor 34 to move the negative lens in a direction that is along the observation luminous fluxes RS and LS.

The observation optical system 30 may also include a configuration for allowing the user U to stereoscopically view the observation object by looking through eyepieces. In this case, the observation optical system 30 may guide the right eye observation luminous flux RS to an eyepiece for the right eye of the user U and guide the left eye observation luminous flux LS to an eyepiece for the left eye of the user U.

The OCT unit 40 will be described. The OCT unit 40 uses the principles of optical coherence tomography (OCT) to acquire an OCT signal (an OCT tomographic image in the present embodiment). In the present embodiment, the OCT unit 40 is incorporated in the observation device 10 of the microscope unit 1. In other words, in the present embodiment, the microscope unit 1 and the OCT unit 40 are integrated. However, the microscope unit 1 and the OCT unit 40 may be separate devices in the observation system 100.

Figure 2:
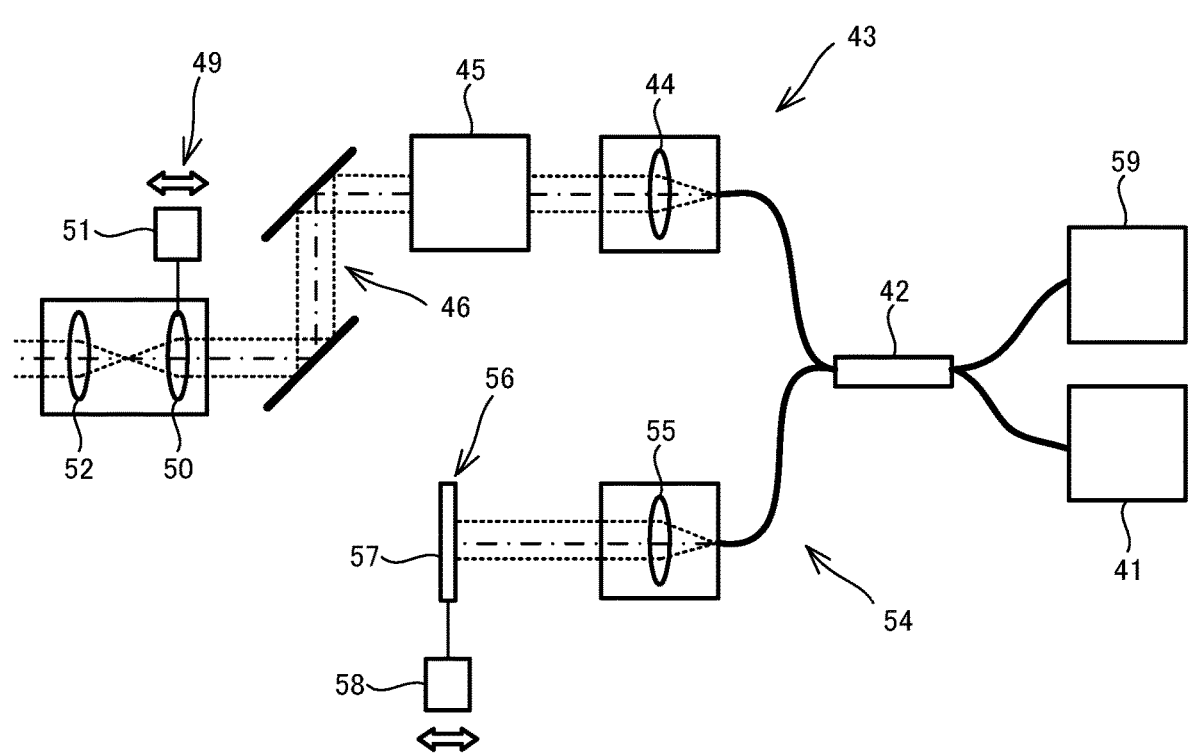
FIG. 2 is a view illustrating a general configuration of an OCT unit 40.

The configuration of an optical system of the OCT unit 40 will be described with reference to FIG. 2. The OCT unit 40 includes an OCT light source 41, a coupler (light splitter) 42, a measurement optical system 43, a reference optical system 54, and an OCT photodetector (detector) 59. The OCT light source 41 emits light (OCT light) to acquire the OCT signal. The coupler 42 splits the luminous flux emitted from the OCT light source 41 into the measurement luminous flux and a reference luminous flux. Further, the coupler 42 of the present embodiment synthesizes the measurement luminous flux reflected by the biological object and the reference luminous flux generated by the reference optical system 54, and causes the synthesized light to be received by the OCT photodetector 59.

The measurement optical system 43 guides the measurement luminous flux split by the coupler 42 to the biological object (the patient's eye E), and returns the measurement luminous flux reflected by the biological object to the coupler 42. In the present embodiment, the measurement optical system 43 includes a collimator lens 44, an NA adjustment unit 45, an optical scanner (a scanning drive unit) 46, a lens 50, and a lens 52, in that order from the upstream side (the OCT light source 41 side) of the optical path. The collimator lens 44 causes the measurement luminous flux that has been split by the coupler 42 and has passed through a fiber to be a parallel luminous flux.

By changing a beam diameter of the measurement luminous flux injected as the parallel luminous flux from the collimator lens 44, the NA adjustment unit 45 adjusts a numerical aperture NA of the measurement luminous flux concentrated toward the biological object. As an example, a known infinity focus zoom system is adopted in the NA adjustment unit 45 of the present embodiment. The control unit 60 controls the drive of a motor (not illustrated) provided in the NA adjustment unit 45 to move a lens provided in the NA adjustment unit 45 in an optical axis direction, thus changing the beam diameter. As a result, the numerical aperture NA of the measurement luminous flux concentrated toward the biological object is adjusted, and a horizontal resolution capacity and a focal depth at the time of acquiring the OCT signal are adjusted.

The optical scanner 46 causes the measurement luminous flux to scan in a two-dimensional direction as a result of being driven by a drive unit. As a result, an acquisition position of the OCT signal on the biological object is determined. The optical scanner 46 of the present embodiment is provided in a position substantially conjugate to the pupil of the patient's eye E. Further, in the present embodiment, two galvanometer mirrors, which can deflect the measurement luminous flux in mutually different directions, are used as the optical scanner 46. However, another device that deflects the light (at least one of a polygon mirror, a resonant scanner, an acousto-optic device, and the like, for example) may be used as the optical scanner 46.

The lens 50 and the lens 52 are provided further to a downstream side (namely, the biological object side) on the optical path of the measurement luminous flux than the optical scanner 46. The lens 50 and the lens 52 function as a projection optical system that projects the measurement luminous flux toward the patient's eye E. The lenses 50 and 52 of the present embodiment are used in a Keplerian telescope. The OCT unit 40 includes an OCT focus adjustment unit 49 that adjusts the focus (hereinafter referred to as the "OCT focus") of the measurement optical system 43 that optically guides the measurement luminous flux. The OCT focus adjustment unit 49 illustrated in FIG. 2 includes the lens 50 of the Keplerian telescope, and an OCT focus adjustment drive motor 51. The OCT focus adjustment drive motor 51 can adjust the OCT focus by moving the lens 50 in a direction that is along the measurement luminous flux.

The reference optical system 54 optically guides the reference luminous flux and returns the reference luminous flux to the coupler 42. The reference optical system 54 of the present embodiment includes a collimator lens 55 and a reference mirror 57. The collimator lens 55 causes the reference luminous flux that has been split by the coupler 42 and has passed through a fiber to be a parallel luminous flux. The reference mirror 57 reflects the reference luminous flux and returns the reference luminous flux to the coupler 42. The configuration of the reference optical system 54 may be changed. For example, the reference optical system 54 may return the reference luminous flux that has been guided from the coupler 42 to the coupler 42 using a transmission type optical system, such as an optical fiber, without reflecting the reference luminous flux.

The OCT unit 40 includes an optical path length difference adjustment unit 56 that adjusts the optical path length difference between the measurement luminous flux and the reference luminous flux. By adjusting the optical path length difference, a range in a depth direction (the Z direction) over which the OCT signal is acquired is changed. The range in the depth direction over which the OCT signal is acquired is, for example, a field of view in the depth direction of the tomographic image, when the tomographic image is acquired. The optical path length difference adjustment unit 56 is provided on at least one of the optical path of the measurement luminous flux and the optical path of the reference luminous flux. The optical path length difference adjustment unit 56 illustrated in FIG. 2 includes the reference mirror 57 and an optical path length difference adjustment drive motor 58. The optical path length difference adjustment drive motor 58 adjusts the optical path length difference by moving the reference mirror 57 in a direction that is along the reference luminous flux. The configuration of the optical path length difference adjustment unit may be changed as appropriate. For example, the optical path length difference adjustment unit may adjust the optical path length difference by moving, in an optical axis direction, the collimator lens 44 provided on the optical path of the measurement luminous flux, and an end portion of the fiber that guides the measurement luminous flux from the coupler 42. Further, the optical path length difference adjustment unit may adjust the optical path length difference by moving, in the optical axis direction, the collimator lens 55 provided on the optical path of the reference luminous flux, and an end portion of the fiber that guides the reference luminous flux from the coupler 42.

The OCT photodetector 59 detects an interference state of the measurement luminous flux and the reference luminous flux. In the case of Fourier-domain OCT, the spectral intensity of an interference light is detected by the OCT photodetector 59, and a depth profile (an A scan signal) of a specified range is acquired by applying a Fourier transform to spectral intensity data. Various types of OCT may be used in the observation system 100. For example, any of spectral-domain OCT (SD-OCT), swept-source OCT (SS-OCT), time-domain OCT (TD-OCT), and the like may be adopted in the observation system 100.

Figure 3:
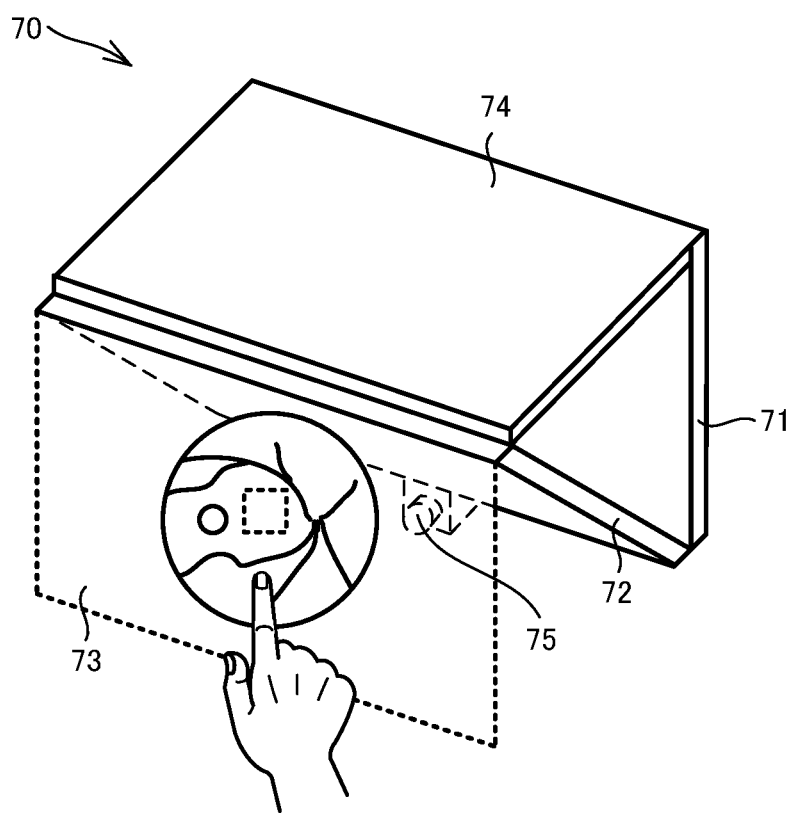
FIG. 3 is a perspective view of an aerial display 70.

Returning now to the description of FIG. 1, the observation system 100 includes an aerial display 70 and a detection unit 75. As illustrated in FIG. 3, the aerial display 70 includes a monitor 71 and an imaging unit 72. The monitor 71 has luminosity and can display various images. The imaging unit (an aerial imaging panel in the present embodiment) 72 causes light beams emitted from a display surface of the monitor 71 to form an image. In this way, the imaging unit 72 causes an aerial image that is an actual image to be displayed on an aerial display region 73. For example, Japanese Re-publication of PCT Publication No. 2009-131128 and PCT Publication No. WO 2014/024677 disclose an optical imaging device and so on that can be used as the imaging unit 72, the relevant portions of which are incorporated by reference. In the present embodiment, the imaging unit 72 is disposed diagonally with respect to a display surface of the monitor 71, by a leading end portion of a support plate 74, which extends to the front from the upper portion of the monitor 71, and the lower portion of the monitor 71. The support plate 74 extends to the front from the upper portion of the monitor 71. As a result of this, the display region 73 is formed in a position that is symmetrical to the display surface of the monitor 71 with the imaging unit 72 as the plane of symmetry. The detection unit 75 detects a position or a movement of an object in the display region 73 in space. As an example, the detection unit 75 of the present embodiment includes a light-emitting portion and a light-receiving portion. The light-emitting portion emits near infrared light. The light-receiving portion receives near infrared light reflected by an object (a hand or a finger of the user, a tool held by the user, or the like, for example) positioned in the display region 73, and detects the position of the object by measuring a phase delay of the received light. By continuously detecting the position of the object, the movement of the object is detected.

The operation unit 69 may be operated by the user U to input various operation commands into the observation system 100. In this embodiment, a foot switch, which is operated by a foot of the user U, is at least provided as the operation unit 69. Therefore, the user U may input various operation commands from the operation unit 69, while handling a surgical instrument or the like with the hand. However, another device (various buttons, a touch panel, or the like, for example) may be used as the operation unit 69, together with the foot switch, or instead of the foot switch.

The control unit 60 controls various operations of the observation system 100 (such as adjustment control of the microscope focus by the microscope focus adjustment unit 32, scanning control of the measurement luminous flux by the OCT unit 40, and adjustment control of the OCT light). The control unit 60 includes a CPU 61, a RAM 62, a ROM 63, and a non-volatile memory (NVM) 64. The CPU 61 is a controller that performs various types of control. The RAM 62 temporarily stores various kinds of information. The ROM 63 stores programs to be executed by the CPU 61, various initial values, and the like. The NVM 64 is a non-transitory storage medium capable of retaining stored content even when the supply of power is cut off. The NVM 64 may store a biological object observation control program for executing biological object observation control processing, which is described below.

In the present embodiment, as an example, the control unit 60 functions as the control unit that performs adjustment control of the microscope focus, scanning control of the measurement luminous flux by the OCT unit 40, adjustment control of the OCT light, and the like. Specifically, in the present embodiment, the control unit 60 functions as a control device that controls the observation system 100. However, the configuration of the control unit that controls the observation system 100 (namely, the control unit that executes a biological object observation control program) may be changed as appropriate. For example, a control unit of a personal computer (not illustrated) connected to the microscope unit 1 may control the observation system 100. Control units provided in individual devices (the control unit 60 and the control unit of the personal computer, for example) may operate in concert to control the observation system 100.

Acquiring Focus State of Observation Optical System

The control unit 60 of the present embodiment can acquire a focus state of the observation optical system 30 of the microscope unit 1 (hereinafter sometimes simply referred to as a "microscope focus state"). As will be described in more detail below, the control unit 60 of the present embodiment sets a target region inside the observation image, in accordance with the position or the movement of the object detected by the detection unit 75 in the display region of the observation image displayed by the aerial display 70. Further, the control unit 60 can automatically adjust the focus of the target region in the observation image in accordance with an acquisition result of the microscope focus state. Here, an example of a method for acquiring the microscope focus state will be described. The control unit 60 of the present embodiment acquires the microscope focus state on the basis of signals from the photodetectors 38R and 38L. Thus, in the observation system 100 of the present embodiment, it is possible to omit a configuration dedicated to acquiring (detecting) the microscope focus state.

As an example, the control unit 60 of the present embodiment acquires the microscope focus state using a contrast detection method. More specifically, the control unit 60 analyzes an image inside the target region, of the observation image (a microscopic image in the present embodiment) captured by the photodetectors 38R and 38L, while changing the microscope focus using the microscope focus adjustment unit 32. The control unit 60 acquires the microscope focus state by causing a position at which the contrast of the image inside the target region is highest to be the position at which the microscope focus is in focus. However, as described above, as a method for acquiring the microscope focus state, a method other than the contrast detection method may be used.

Biological Object Observation Control Processing

Below, biological object observation control processing performed by the control unit 60 of the observation system 100 will be described. The CPU 61 of the control unit 60 performs the biological object observation control processing illustrated in FIG. 4, in accordance with the biological object observation control program stored in the NVM 64.

First, the CPU 61 starts advance processing (S1). As described above, the CPU 61 captures an image of the patient's eye E using the photodetectors 38R and 38L of the observation optical system 30. In the advance processing, the CPU 61 starts display of the observation image on the display 67, on the basis of the signals from the photodetectors 38R and 38L. In this case, the CPU 61 may acquire the microscope focus state in a region set in advance (a region in the center of the screen, for example). Then, the CPU 61 may adjust the microscope focus such that the microscope focus state becomes favorable. Further, the CPU 61 may place the microscope focus at a center point of an adjustable range and may start the image capture and the display of the observation image, without acquiring the microscope focus state. Further, the CPU 51 adjusts the optical path length difference in the OCT unit 40 on the basis of an optical parameter of the observation optical system 30. For example, a case is illustrated in which the objective lens 31 whose focal length can be changed is used, and the focal length is changed from 170 mm to 200 mm. In this case, a distance from the objective lens 31 to the patient's eye E (a working distance) also becomes approximately 30 mm longer. Thus, the CPU 51 controls the driving of the optical path length difference adjustment unit 56 on the basis of the optical parameter (the focal length) of the observation optical system 30, and causes the optical path length difference to change by approximately 30 mm.

Next, the CPU 61 acquires a most recent observation image captured by the photodetectors 38R and 38L and causes the aerial display 70 to display the observation image (S2). The CPU 61 detects the object (such as the user's finger or the like) in the display region 73 in space, using the detection unit 75 (S3). If the position or the movement of the object used to specify a region of interest in the display region 73 in space is not detected (no at S6), the processing moves to S30 without any other processing. When the position or the movement of the object used to specify the region of interest is detected (yes at S6), the CPU 61 performs the microscope focus adjustment control, the scanning control of the measurement luminous flux by the OCT unit 40, and the adjustment control of the OCT light in accordance with the position or movement of the detected object (S9 to S24).

First, the CPU 61 sets the target region in the observation image in accordance with the position or the movement of the object detected in the display region 73 (S9). Next, the CPU 61 acquires the microscope focus state (S10). As described above, the CPU 61 of the present embodiment acquires the microscope focus state in the target region on the basis of the signal from the photodetectors 38R and 38L in the set target region. Next, the CPU 61 adjusts the focus of the target region in the observation image, by controlling the driving of the microscope focus adjustment drive unit 32 on the basis of an acquired result of the microscope focus state (S11). Further, the CPU 61 sets a scanning position of the measurement luminous flux by the OCT unit 40 in accordance with the position or the movement of the object detected in the display region 73 (S12).

The above processing will be described specifically, with reference to FIG. 5 to FIG. 9. In the aerial display region 73 formed by the aerial display 70, a state is illustrated in which an observation image 15 of an ocular fundus is displayed. In the observation image 15 illustrated in FIG. 5 to FIG. 9, tissues of an optic disc 77, a macula lutea 78, a fundus oculi blood vessel 79, and the like are shown. Further, a region of interest 81, which is described below, includes not only a region but also a point and a line.

First, with reference to FIG. 5 and FIG. 6, an example will be described of processing when the region of interest 81 specified by the user is a point. In the example illustrated in FIG. 5 and FIG. 6, the region of interest 81 that is the point is specified by the user positioning the user's finger or the like on a single point in the observation image 15 displayed in the display region 73. In this case, the CPU 61 sets, as a target region 82, a region including the region of interest 81 that is the point (S9). In the example illustrated in FIG. 5, a rectangular region that centers on the detected region of interest 81 that is the point is set as the target region 82. The shape of the target region 82 is not limited to the rectangular shape. The size of the target region 82 may be set in advance. The size of the target region 82 may be set in accordance with a command from the user (an operation command by the operation unit 69, for example).

Figure 6:
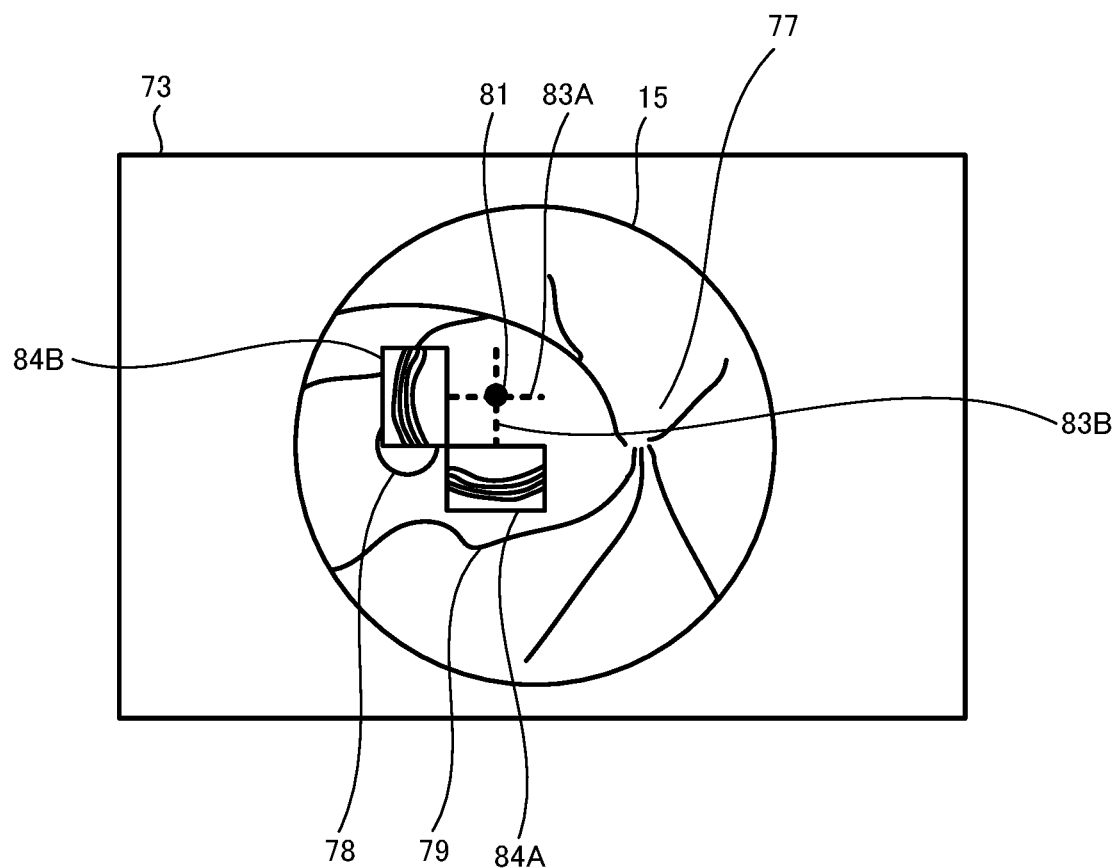
FIG. 6 is a view illustrating an example of scanning positions 83A and 83B, when the region of interest 81 that is the point is specified on the observation image 15.

Further, as illustrated in FIG. 6, the CPU 61 sets scanning positions 83A and 83B of the measurement luminous fluxes by the OCT unit 40, on the basis of the position of the detected region of interest 81 that is the point (S12). In the example illustrated in FIG. 6, the set two line-shaped scanning positions 83A and 83B traverse the region of interest 81 that is the point and are orthogonal to each other. It goes without saying that the number of the scanning positions 83 is not limited to two. The CPU 61 causes a two-dimensional tomographic image 84A, which is captured by causing the measurement luminous flux to scan the scanning position 83A, to be displayed alongside the scanning position 83A. Further, the CPU 61 causes a two-dimensional tomographic image 84B, which is captured by causing the measurement luminous flux to scan the scanning position 83B, to be displayed alongside the scanning position 84B.

Further, the user can switch between display and non-display of the two-dimensional tomographic images 84A and 84B in the display region 73, by performing a specific movement using the user's finger or the like in the display region 73. In the present embodiment, when a movement of the finger or the like is detected that traverses the displayed two-dimensional tomographic images 84A and 84B (a swipe gesture is performed), the CPU 61 causes the two-dimensional tomographic images 84A and 84B displayed on the traversed position not to be displayed. Further, when a similar movement is once more detected, the CPU 61 causes the two-dimensional tomographic images 84A and 84B to be displayed in the display region 73. Thus, the user can easily switch between the display and non-display of the two-dimensional tomographic images 84A and 84B by performing the specific operation with respect to the observation image 15 displayed in the display region 73.

Figure 7:
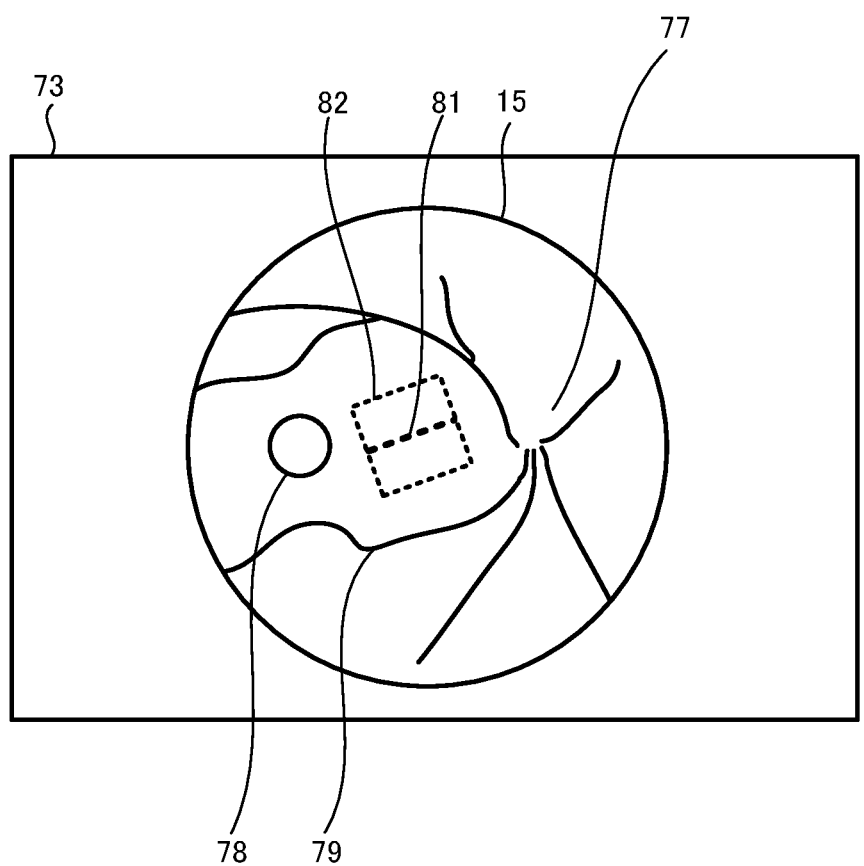
FIG. 7 is a view illustrating an example of the target region 82, when the region of interest 81 that is a line is specified on the observation image 15.
Figure 8:
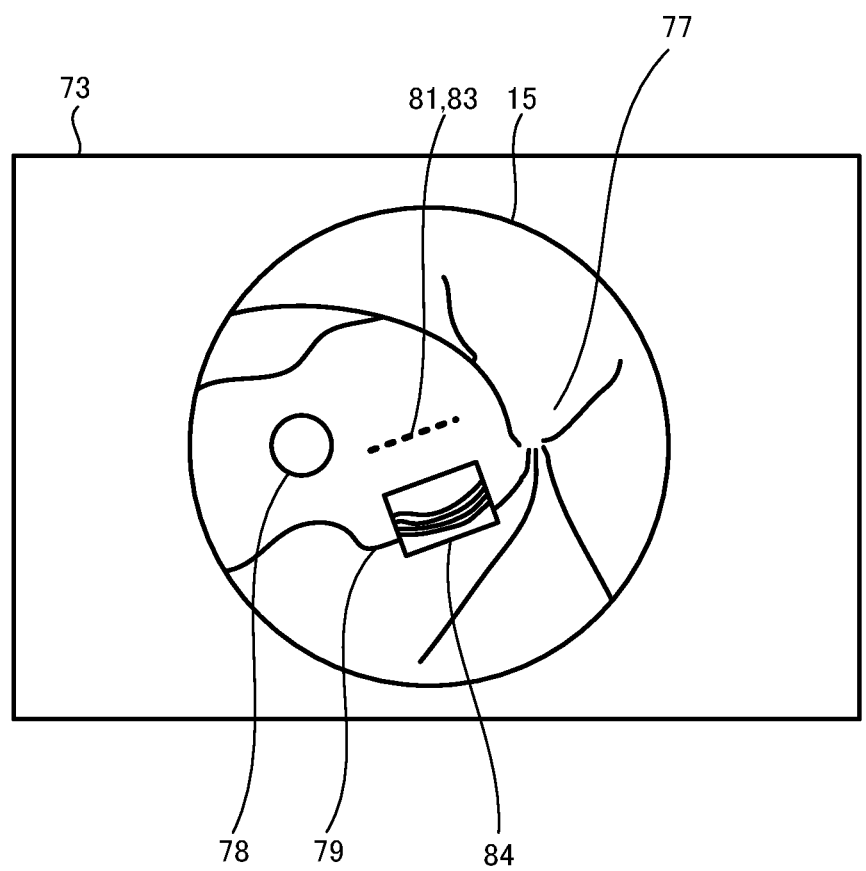
FIG. 8 is a view illustrating an example of a scanning position 83, when the region of interest 81 that is the line is specified on the observation image 15.

With reference to FIG. 7 and FIG. 8, an example will be described of processing when the region of interest 81 specified by the user is a line. In the example illustrated in FIG. 7 and FIG. 8, the user may specify the region of interest 81 that is the line by moving the user's finger or the like in a line shape (performing the swipe gesture) on the observation image 15 displayed in the display region 73. In this case, the CPU 61 sets, as the target region 82, a region including the region of interest 81 that is the line (S9). In the example illustrated in FIG. 7, the rectangular target region 82 is set for which one side is the same length as the detected line-shaped region of interest 81 and that has a symmetrical shape centering on the line-shaped region of interest 81. Similarly to the example illustrated in FIG. 5 and FIG. 6, the shape, the size, and so on of the target region 82 may be changed as necessary.

Further, as illustrated in FIG. 8, the CPU 61 sets the scanning position 83 of the measurement luminous flux by the OCT unit 40 on the basis of the position of the detected region of interest 81 that is the line (S12). In the example illustrated in FIG. 8, the scanning position 83 is set on the region of interest 81 that is the line. The user may specify a plurality of regions of interest 81 and scanning positions 83. In addition, in the example illustrated in FIG. 8, the lengths of the region of interest 81 and the scanning position 83 are limited by a length that is equal to or less than a scan range of the measurement luminous flux. The CPU 61 causes a two-dimensional tomographic image 84, which is captured by causing the measurement luminous flux to scan the scanning position 83, to be displayed alongside the scanning position 83. Further, using the same method as the method illustrated in FIG. 5 and FIG. 6, the CPU 61 can switch between the display and the non-display of the two-dimensional tomographic image 84.

Figure 9:
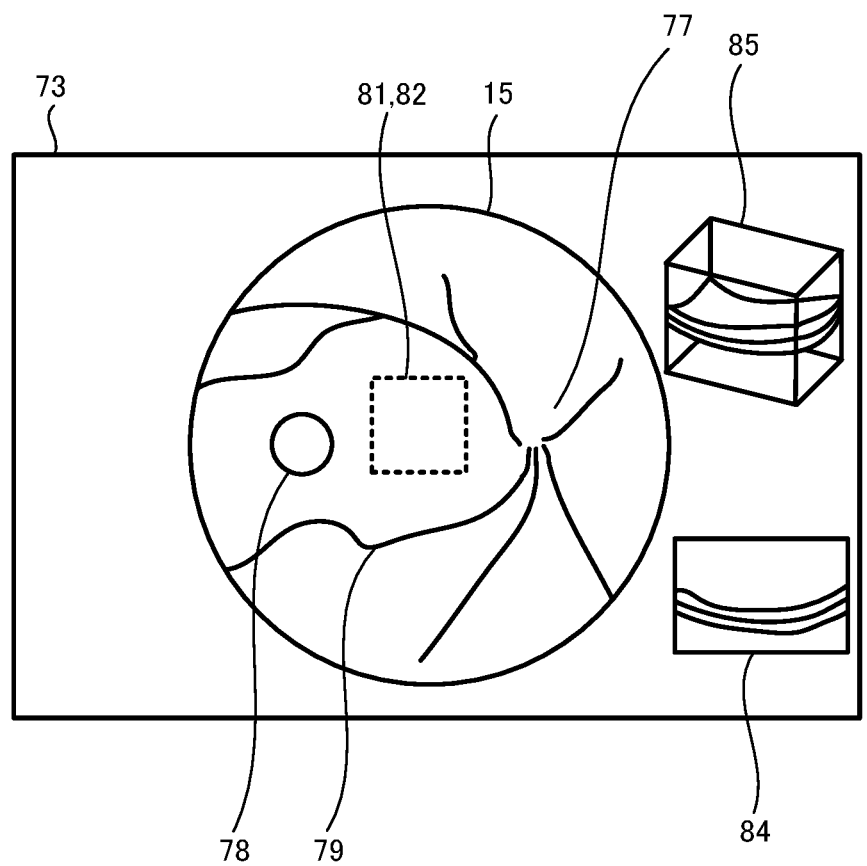
FIG. 9 is a view illustrating an example of the target region 82, when the region of interest 81 that is a surface is specified on the observation image 15.

With reference to FIG. 9, an example will be described of processing when the region of interest 81 specified by the user is a surface. A method for the user to specify the region of interest 81 that is the surface may be selected as appropriate. For example, when specifying the quadrilateral region of interest 81, the user may move the user's finger or the like on the observation image 15 so as to follow along at least one diagonal line thereof. When specifying the quadrilateral region of interest 81, the user may position the user's finger or the like on at least two of the four vertices of the region of interest 81 to be specified (two vertices positioned diagonally with respect to each other, for example). A specific movement may be provided to distinguish between the regions of interest 81 that are the point and the line and the region of interest 81 that is the surface. For example, when causing the user to specify a start point of the diagonal line, or the vertices, the CPU 61 may require the user to perform a movement to specify the same point a plurality of times. In the example illustrated in FIG. 9, the target region 82 is set that is the same region as the detected region of interest 81 that is the surface (S9). However, the region of interest 81 and the target region 82 need not necessarily be the same region.

The CPU 61 sets the scanning position of the measurement luminous flux by the OCT unit 40 on the basis of the position of the detected region of interest 81 that is the surface (S12). In the example illustrated in FIG. 9, the scanning position (not illustrated) is set of a raster scan in order to acquire a three-dimensional tomographic image 85 in the region of interest 81 that is the surface. The CPU 61 can cause the three-dimensional tomographic image 85 captured by performing the raster scan of the measurement luminous flux in the region of interest 81 to be displayed in the display region 73. Further, the CPU 61 can cause at least one of a plurality of the two-dimensional tomographic images 84 captured in the region of interest 81 to be displayed in the display region 73.

Figure 5:
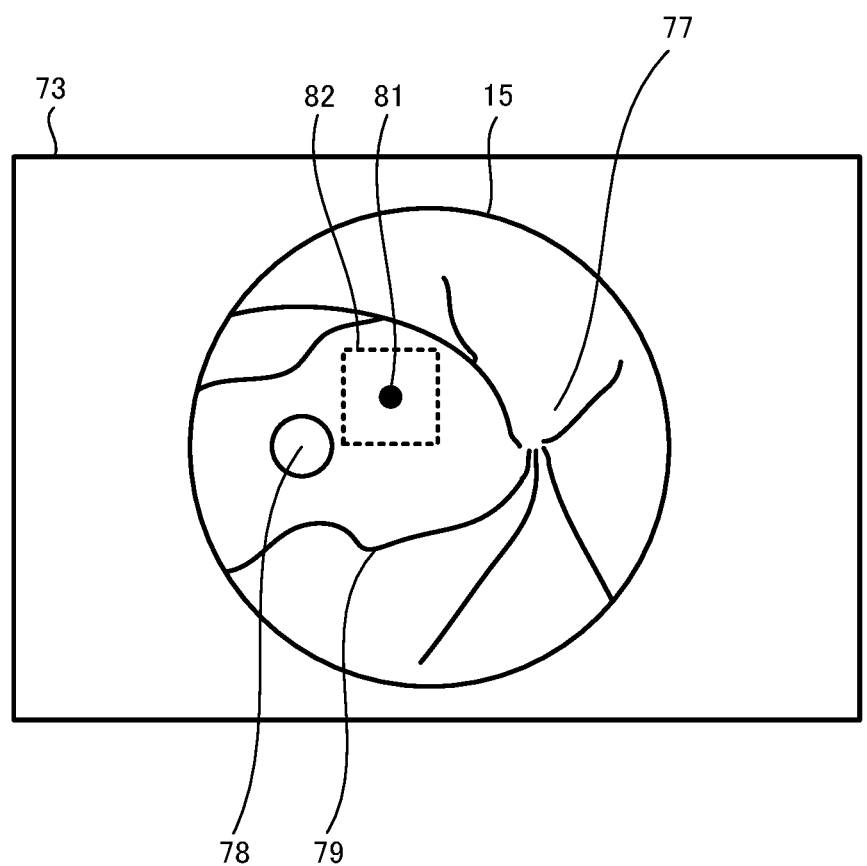
FIG. 5 is a view illustrating an example of a target region 82, when a region of interest 81 that is a point is specified on an observation image 15.

Using the same method as the method illustrated in FIG. 5 and FIG. 6, the CPU 61 can switch between the display and the non-display of the two-dimensional tomographic image 84. Further, the CPU 61 can change an orientation of the three-dimensional tomographic image 85 in accordance with the position or the movement of the object detected on the three-dimensional tomographic image 85 displayed in the display region 73. For example, when a movement of the object from the left to the right (a left-to-right swipe gesture) is detected on the three-dimensional tomographic image 85, the CPU 61 rotates the displayed three-dimensional tomographic image 85 from the left to the right (namely, in the counter-clockwise direction as seen from above). Thus, the user can easily adjust the orientation of the displayed three-dimensional tomographic image 85 to an appropriate orientation.

Figure 10:
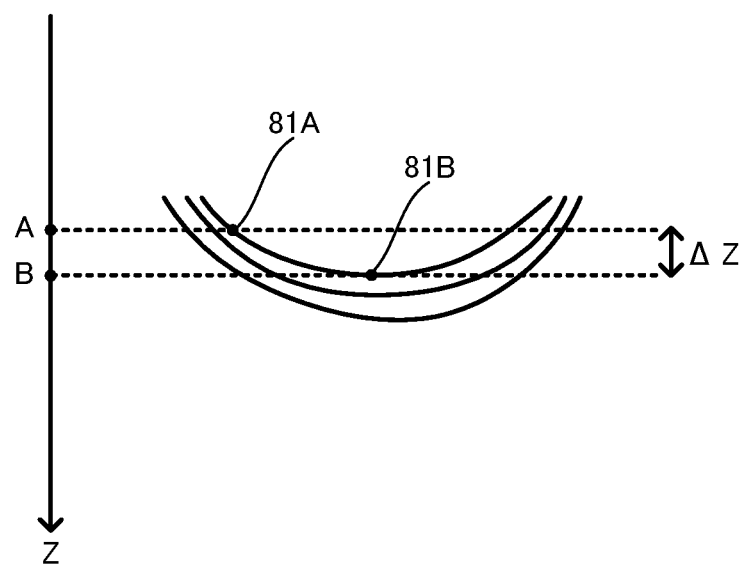
FIG. 10 is an explanatory view illustrating a manner in which a position of a microscope focus in a depth direction changes in accordance with a change in the region of interest 81.

Processing to adjust the microscope focus (S11) will be described with reference to FIG. 10. In the example illustrated in FIG. 10, when the user changes a region of interest 81A to a region of interest 81B, even without movement of the patient's eye E, an appropriate position of the microscope focus in the Z direction moves by $\Delta Z$ in the positive Z direction. In this case, the CPU 61 controls the microscope focus adjustment drive motor 34 such that the focus of the target region set on the basis of the changed region of interest 81B is in focus. Thus, the focus of the position to which the user desires to pay attention can be appropriately focused.

Further, at step S11, the CPU 61 can adjust the focus on the basis of an offset amount input by the user. In the present embodiment, the user can input an offset amount (a deviation amount) in a direction along the optical axis of a desired focus position, with respect to a normal focus position at which focusing is performed on the basis of the acquired result of the microscope focus state. The normal focus position is a focus position that is focused by automatic focusing when the offset amount is zero. An input method of the offset amount may be selected as appropriate. For example, a method may be adopted in which the user is prompted to select one from among "No offset," "Focus in front of the subject," and "Focus behind the subject." Alternatively, a method may be adopted in which the user is prompted to input a positive or a negative deviation amount value, where "0" is no offset. When the offset amount is input, the CPU 61 performs focusing on the position that deviates by the input offset amount from the normal focus position that is based on the acquisition result of the microscope focus state (in the present embodiment, the focus position at which the contrast of the target region 82 is optimal).

Figure 4:
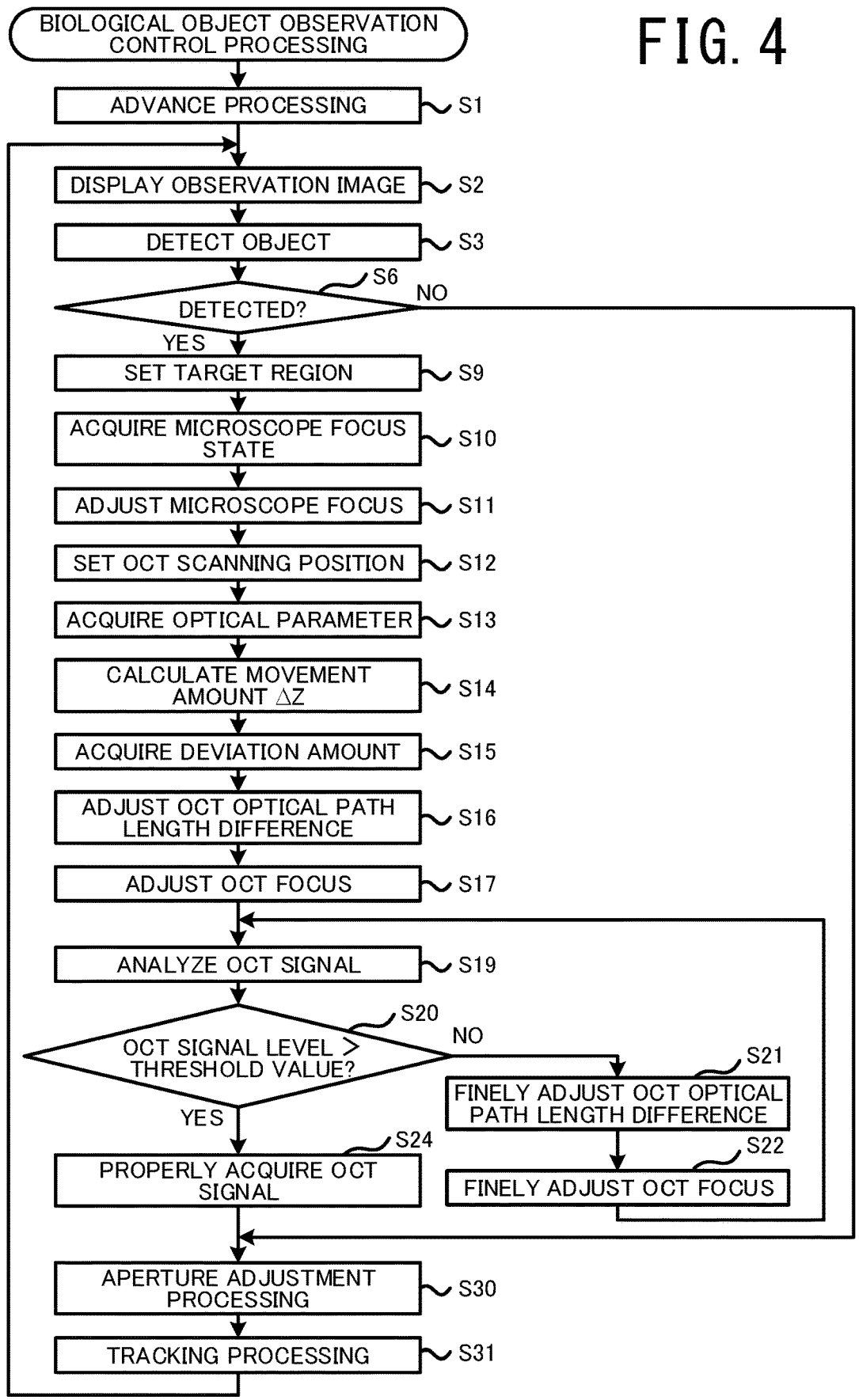
FIG. 4 is a flowchart illustrating an example of biological object observation control processing.

Returning now to the description of FIG. 4, the CPU 61 performs processing to adjust the OCT light in accordance with the change in the microscope focus state in the target region 82 (S13 to S17). As an example, the CPU 61 of the present embodiment calculates the movement amount $\Delta Z$ in a depth direction (the Z direction) of an observation position (the position at which the microscope focus is focused), on the basis of the optical parameter of the observation optical system 30 (including the microscope focus adjustment unit 32) and a drive amount of the microscope focus adjustment unit 32. The CPU 61 adjusts the OCT light on the basis of the movement amount $\Delta Z$. This will be described in more detail below.

First, the CPU 61 acquires the optical parameter of the observation optical system 30 (S13). In the present embodiment, the focal length of the observation optical system 30 that is changed by the microscope focus adjustment unit 32 is acquired. Further, in the present embodiment, the optical parameter changes depending on whether the wide angle observation unit 27 (see FIG. 1) is used. Thus, the CPU 61 of the present embodiment acquires the optical parameter in accordance with the presence or absence of the wide angle observation unit 27. In a specific example, in the present embodiment, the CPU 61 acquires, as the optical parameters of the observation optical system 30, an imaging magnification $\beta_1$ and a longitudinal magnification $\alpha_1$ for the observation object in relation to an intermediate image plane of the observation optical system 30 (a front side focal position of the front lens 29) (, which change depending on whether the wide angle observation unit 27 is used and in accordance with the focal length). Further, in the present embodiment, the CPU 61 acquires a focal position of the lens 50 of the front group of the Keplerian telescope of the OCT unit 40 with respect to the observation object, namely, acquires an imaging magnification $\beta_2$ and a longitudinal magnification $\alpha_2$ for an intermediate image of an end face of the fiber.

Next, on the basis of the change in the microscope focus state, the CPU 61 calculates the amount $\Delta Z$ by which a position to be observed has moved in the Z direction (S14). For example, in the example shown in FIG. 10, the microscope focus is adjusted by the microscope focus adjustment unit 32 as a result of the position to be observed moving from 81A to 82B. Thus, the CPU 61 can calculate the movement amount $\Delta Z$ of the position to be observed, on the basis of the drive amount of the microscope focus adjustment unit 32. In the example shown in FIG. 10, if the movement amount of the microscope focus with respect to the position of the intermediate image is denoted by $\Delta Z_1$, then $\Delta Z = \alpha_1 \times \Delta Z_1 = \beta_1^2 \times \Delta Z_1$ is obtained. The movement amount of the microscope focus with respect to the position of the intermediate image matches an extending amount of the objective lens 31 and the reducing lens 28 of the microscope focus adjustment unit 32.

Next, the CPU 61 acquires a deviation amount in the depth direction (the Z direction) along the luminous flux between an observation target position that is a reference for focusing a microscope focus Sf and an OCT target position that is a reference for acquiring an OCT signal (S15). The OCT target position is at least one of a target position that is a reference for focusing a zero delay position (a position at which the optical path length difference of the OCT light is zero) and a target position that is a reference for focusing an OCT focus Of. In the observation system 100 of the present embodiment, the user may independently specify the observation target position and the OCT target position in the depth direction by inputting a command to the operation unit 69 or the like. When the observation target position and the OCT target position are aligned in the depth direction, the deviation amount acquired at S15 is zero.

Next, by driving the optical path length difference adjustment unit 56 of the OCT unit 40, on the basis of the movement amount $\Delta Z$ of the position to be observed in the Z direction, the CPU 61 adjusts the optical path length difference (S16). In the present embodiment, the CPU 61 controls the drive of the optical path length difference adjustment drive motor 58 of the optical path length difference adjustment unit 56 to move the reference mirror 57 by $\Delta Z \times n_g$ (where $n_g$ is a group refractive index of the patient's eye E), thus adjusting the optical path length difference. For example, in the example shown in FIG. 10, the optical path length difference is adjusted in accordance with the change of the microscope focus. As a result of this, an acquisition range of the OCT signal centered on a point A in the Z direction is changed to an acquisition range of the OCT signal centered on a point B. When there is the deviation between the observation target position and the target position for focusing the zero delay position, the CPU 61 drives the optical path length difference adjustment unit 56 while taking into account the deviation amount acquired at S15. Thus, even when there is deviation between the observation target position and the target position for focusing the zero delay position, the optical path length difference can be appropriately adjusted.

Next, by driving the OCT focus adjustment unit 49 on the basis of the movement amount $\Delta Z$ of the position to be observed, the CPU 61 adjusts the OCT focus (S17). In the present embodiment, as shown in FIG. 1, the measurement luminous flux of the OCT also passes through the microscope focus adjustment unit 32. Thus, when the microscope focus adjustment unit 32 is driven, the OCT focus also moves. However, due to a wavelength difference and the like between the observation light of the microscope unit 1 and the OCT light, there may be a case in which the movement amount of the microscope focus and the movement amount of the OCT focus in relation to the drive amount of the microscope focus adjustment unit 32 do not match each other. Thus, the CPU 61 of the present embodiment more accurately adjusts the OCT focus by also driving the OCT focus adjustment unit 49 in accordance with the change in the microscope focus state.

The drive amount of the OCT focus adjustment unit 49 can be calculated on the basis of an optical parameter of the measurement optical system 43 and the like. As an example, if the movement amount of the OCT focus at the intermediate image position is denoted by $\Delta Z_2$, the imaging magnification of the measurement optical system 43 is denoted by $\beta_2$, the longitudinal magnification is denoted by $\alpha_2$, and the drive amount of the OCT focus adjustment unit 49 (the movement amount of the lens 52 in the present embodiment) is denoted by $\Delta Z_3$, then $\Delta Z_2 = \alpha_2 \times \Delta Z_3 = \beta_2^2 \times \Delta Z_3$ is obtained. $\Delta Z_2$ is determined in accordance with the movement amount $\Delta Z$ of the position to be observed that is calculated at S14, and thus, from the above-described formula, the drive amount of the OCT focus adjustment unit 49 can be calculated. When there is the deviation between the observation target position and the target position for focusing the OCT focus Of (as in FIG. 6 and FIG. 7, for example), the CPU 61 drives the OCT focus adjustment unit 49 while also taking into account the deviation amount acquired at S15.

By the processing from S13 to S17 being performed as described above, the adjustment of the OCT light is performed in accordance with the change in the microscope focus state in the target region 82. As a result, the optical path length difference and the OCT focus of the OCT unit 40 can be rapidly and easily adjusted. Here, the OCT light may be adjusted only in accordance with the change in the microscope focus state, but the CPU 61 of the present embodiment also adjusts the OCT light on the basis of an analysis result of the OCT signal (S19 to S22). As a result, the adjustment of the OCT light can be more appropriately adjusted. This will be described in detail below.

First, the CPU 61 temporarily acquires the OCT signal via the OCT photodetector 59 and analyzes the OCT signal (S19). Next, the CPU 61 determines whether the level of the analyzed OCT signal is greater than a threshold value (S20). When the level of the OCT signal is equal to or less than the threshold value (NO at S20), the CPU 61 drives the optical path length difference adjustment unit 56 to finely adjust the optical path length difference (S21). Further, the CPU 61 drives the OCT focus adjustment unit 49 to finely adjust the OCT focus (S22). The processing returns to S19 and the processing from S19 to S22 is repeated until the level of the OCT signal is greater than the threshold value. Since the optical path length difference and the OCT focus are generally appropriately adjusted in accordance with the change in the microscope focus state, a range of the adjustment on the basis of the analysis result of the OCT signal (S19 to S22) can be made narrower. Thus, the OCT light can be rapidly and appropriately adjusted. When the level of the OCT signal becomes greater than the threshold value (YES at S20), the CPU 61 properly acquires the OCT signal (S24).

The method for analyzing the OCT signal may be selected as appropriate. For example, the CPU 61 may analyze signals for the whole of the acquired OCT image. Alternatively, of the acquired OCT image, the CPU 61 may analyze a signal for a specified range centered on the region of interest 81. In this case, the quality of the OCT image in the range that includes the region of interest 81 can be further improved. Of the acquired OCT image, the CPU 61 may carry out weighting such that the analysis result in the vicinity of the region of interest 81 is accorded more significance than an analysis result of a position separated from the region of interest 81.

Next, the CPU 61 performs processing to adjust the aperture in accordance with a detection result by the detection unit 75 (S30). More specifically, when a command to adjust the adjustable aperture 36 is detected by the detection unit 75, the CPU 61 drives the aperture drive unit 37 in accordance with the command, and adjusts the opening diameter of the adjustable aperture 36. An input method of the command to adjust the adjustable aperture 36 may be selected as appropriate. For example, the opening diameter of the adjustable aperture 36 may be made smaller when the object is detected in the same position as the once set region of interest 81, of the observation image 15 displayed in the display region 73. For example, depending on the biological object or the like that is the subject, it may be difficult to appropriately perform the auto focusing of the observation image at S11. When the auto focusing is not appropriately performed, the user can make the focal depth deeper and make it easier to align the focus, by inputting a command to make the adjustable aperture 36 smaller. In contrast, the user can make the brightness of the range being viewed brighter, by inputting a command to make the adjustable aperture 36 larger.

Next, the CPU 61 performs tracking processing of the target region 82 (S31) and returns the processing to S2. The tracking processing of the target region 82 is processing in which the position of the target region 82 is caused to follow (track) in accordance with the movement of the detected subject. As an example, the CPU 61 of the present embodiment performs image processing on the observation image 15 captured by the photodetectors 38R and 38L, and thus detects the movement of the subject captured in the observation image 15. For example, by performing the image processing, the CPU 61 may detect a specific portion of the biological object (at least one of the optic disc 77, the macula lutea 78, and the fundus oculi blood vessel 79, for example), and may detect the movement of the subject by detecting the movement of the specific part. Further, when the wide angle observation unit 27 (see FIG. 1) is used, the CPU 61 may detect the movement of the subject by detecting a movement in the position of the front lens 29 provided in the wide angle observation unit 27 (a position of an opening of the front lens 29, for example). The CPU 61 causes the position of the target region 82 to track in accordance with the detected movement of the subject. As a result of this, even if the subject moves, the quality of the observation image 15 in the target region can be favorably maintained. The CPU 61 also performs processing to cause the scanning position of an OCT measurement luminous flux to track in accordance with the detected movement of the subject.

As described above, in the present embodiment, the user can easily and appropriately input the command to adjust the observation state, by directly moving the user's finger to a desired position on the observation image 15 displayed in the display region 73. The CPU 61 adjusts the observation state using at least one of the detected position information and the detected movement information, and can thus accurately perform the adjustment that matches the user's desire.

The biological object observation system 100 of the present embodiment may have a function to automatically perform display control of specific information in the display region of the aerial display 70. More specifically, the biological object observation system 100 may be provided with a patient detection unit (a pressure sensor or the like arranged on a treatment table, for example), which detects whether the patient is present on the treatment table (an operating table, for example). When the patient detection unit detects that the patient is present on the treatment table, the CPU 61 may start the display on the aerial display 70 of the specific information that is information or the like that is not desired to be disclosed to the patient. Further, when it is detected that the patient has moved away from the treatment table, the CPU 61 may stop the display of the specific information in the aerial display 70. As a result of this, the specific information may be automatically and appropriately displayed in the aerial display 70.

The technology disclosed in the above-described embodiment is merely an example. Thus, the technology illustrated in the above-described embodiment may be modified. For example, only part of the techniques disclosed in the above-described embodiment may be performed. In the above-described embodiment, the adjustment processing of the microscope focus of the microscope unit 1 and the setting processing of the scanning position of the measurement luminous flux by the OCT unit 40 are performed on the basis of the detection result of the object on the observation image 15 displayed in the aerial display 70. However, only one of the adjustment processing of the microscope focus of the microscope unit 1 and the setting processing of the scanning position of the measurement luminous flux by the OCT unit 40 may be performed on the basis of the detection result by the detection unit 75. The observation system may include one of the microscope unit 1 and the OCT unit 40. Further, at least part of the above-described techniques disclosed in the above-described embodiment may be applied to a device other than a surgical microscope and an OCT device. For example, in various devices that perform image capture of a biological object, a position that is a reference for driving an optical system that defines an image capture range or a position that is a reference for focusing a focus of a captured image may be set on the basis of a detection result of an object on an observation image. In the case of the field of ophthalmology, the various devices that perform the image capture of the biological object may include, for example, a eye fundus camera, a scanning laser ophthalmoscope, an infrared camera, and the like. Further, an image capture range of a motion contrast image acquired by the OCT unit 40 may be set on the basis of the detection result of the object on the observation image. The motion contrast image is an image showing a movement in tissue (the blood flow flowing through a vessel of the tissue, the flow of lymph fluid in the tissue, or the like, for example). The CPU 61 may acquire the motion contrast image by acquiring OCT signals, at different timings, from the same position on the tissue, and performing processing on the acquired OCT signals.

The photodetectors 38R and 38L of the above-described embodiment capture the observation image 15 by receiving the measurement luminous flux guided by the observation optical system 30 of the microscope unit 1. However, the method for acquiring the observation image of the biological object may be changed. For example, in the OCT device, a front image capture unit that captures a front image of the subject may be separately provided from the OCT unit. In this case, an imaging element of the front image capture unit may capture the observation image. Alternatively, an Enface image obtained from OCT signals acquired by an OCT photodetector may be used as the observation image. In this case, the OCT photodetector may function as a photodetector to receive optical information for generating the observation image.

Further, in the above-described embodiment, the adjustment of the optical path length difference and the adjustment of the OCT focus in the OCT unit 40 are performed in accordance with a change in the microscope focus state in the target region 82. However, one of the adjustment of the optical path length difference and the adjustment of the OCT focus may be performed. In addition, the adjustment of the OCT light need not necessarily be performed in concert with the change in the microscope focus state. Further, in the above-described embodiment, the fine adjustment of the OCT optical path length difference (S21) and the fine adjustment of the OCT focus (S22) are performed in accordance with the analysis result of the OCT signal. However, the processing at at least one of S21 and S22 may be omitted.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A biological object observation system comprising:
   an observation optical unit including an optical system that guides a luminous flux from a biological object that is an object to be observed and a drive unit that drives the optical system;
   a photodetector receiving optical information in accordance with the biological object;
   an aerial display displaying an observation image of the biological object generated on the basis of the optical information received by the photodetector, the aerial display including:
      a monitor displaying an image; and
      an imaging unit that displays an aerial image in space by causing light beams emitted from a display surface of the monitor to form an image, the aerial image being an actual image;

a detection unit detecting at least one of a position and a movement of an object that a user moves into a display region of the observation image displayed by the aerial display; and a processor programmed to:
  detect the at least one of the position and the movement of the object via the detection unit, and
  control the drive unit of the optical system in accordance with the detected at least one of the position and the movement of the object in the display region of the observation image displayed by the aerial display.

2. The biological object observation system according to claim 1, wherein
  the observation optical unit includes an optical coherence tomography (OCT) unit including:
    an OCT light source;
    a light splitter splitting a luminous flux emitted from the OCT light source into a measurement luminous flux and a reference luminous flux;
    a scanning drive unit being the drive unit that causes the measurement luminous flux split by the light splitter to scan on the biological object; and
    an OCT photodetector receiving interference light obtained by synthesis of the reference luminous flux and the measurement luminous flux reflected by the biological object, and
  the processor controls the scanning drive unit of the OCT unit, in accordance with the at least one of the position and the movement of the object detected, in the display region of the observation image, by the detection unit.

3. The biological object observation system according to claim 1, wherein
  the observation optical unit includes a microscope unit including:
    a microscope optical system being the optical system that guides an observation luminous flux allowing a user to observe the magnified biological object; and
    a microscope focus adjustment drive unit being the drive unit that adjusts a focus of the microscope optical system, the microscope focus adjustment drive unit being provided on a light path of the observation luminous flux in the microscope optical system,
  the photodetector captures the observation image by receiving the observation luminous flux guided by the microscope optical system, and
  the processor is further programmed to:
    set a target region on the observation image captured by the photodetector, on the basis of the at least one of the position and the movement of the object, in the display region of the observation image, detected by the detection unit,
    acquire a focus state of the microscope optical system, and
    adjust a focus of the target region in the observation image by driving the microscope focus adjustment drive unit on the basis of an acquisition result of the focus state of the microscope optical system.

4. The biological object observation system according to claim 3, wherein
  the observation optical unit includes optical coherence tomography (OCT) unit including:
    an OCT light source;
    a light splitter splitting a luminous flux emitted from the OCT light source into a measurement luminous flux and a reference luminous flux;
    a scanning drive unit being the drive unit that causes the measurement luminous flux split by the light splitter to scan on the biological object;
    an OCT photodetector receiving interference light obtained by synthesis of the reference luminous flux and the measurement luminous flux reflected by the biological object, and
    an OCT light adjustment drive unit adjusting at least one of an optical path length difference between the measurement luminous flux and the reference luminous flux and a focus of an optical system that guides the measurement luminous flux, the OCT light adjustment drive unit being provided on at least one of an optical path of the measurement luminous flux and an optical path of the reference luminous flux, and
  the processor is further programmed to:
    control the scanning drive unit in accordance with the at least one of the position and the movement of the object, in the display region of the observation image, detected by the detection unit, and
    drive the OCT light adjustment drive unit in accordance with a change in the focus state of the microscope optical system.

5. The biological object observation system according to claim 3, wherein the processor acquires the focus state of the microscope optical system on the basis of a signal in the set target region, among signals from the photodetector.

6. The biological object observation system according to claim 3, wherein
  the processor is further programmed to:
    detect a movement of a subject captured in the observation image by performing image processing on the observation image captured by the photodetector, and
    cause a position of the target region in the observation image to track in accordance with the detected movement of the subject.

7. The biological object observation system according to claim 3, wherein
  the microscope unit further includes:
    an adjustable aperture adjusting a luminous flux diameter of the observation luminous flux, the adjustable aperture being provided on an optical path of the observation luminous flux in the microscope optical system; and
    an aperture drive unit driving the adjustable aperture, and
  the processor controls the aperture drive unit in accordance with the at least one of the position and the movement of the object, in the display region of the observation image, detected by the detection unit.

8. A non-transitory computer-readable medium storing computer-readable instructions for use with a biological object observation system including:
  an observation optical unit including an optical system that guides a luminous flux from a biological object and a drive unit that drives the optical system;
  a photodetector receiving optical information in accordance with the biological object;
  an aerial display displaying an observation image of the biological object generated on the basis of the optical information received by the photodetector, the aerial display including: (a) a monitor displaying an image, and (b) an imaging unit that displays an aerial image in space by causing light beams emitted from a display surface of the monitor to form an image, the aerial image being an actual image; and a detection unit detecting at least one of a position and a movement of an object that a user moves into a display region of the observation image displayed by the aerial display, the computer-readable instructions causing a processor of the biological object observation system to perform steps comprising:

detecting the at least one of the position and the movement of the object via the detection unit, and controlling the drive unit of the observation optical unit in accordance with the detected at least one of the position and the movement of the object, in the display region of the observation image displayed by the aerial display.

9. A biological object observation system for use with a biological object, the biological object observation system comprising:

an optical system that guides a luminous flux emitted from the biological object that is an object to be observed;

a drive motor configured to drive the optical system;

a photodetector configured to detect optical information from the biological object;

an aerial display displaying an observation image of the biological object generated based on the detected optical information, the aerial display including:

a monitor displaying an image; and an imaging panel that displays an aerial image in space by causing light beams emitted from a display surface of the monitor to form an image, the aerial image being an actual image;

a detector detecting at least one of a position and a movement of an object that a user moves into a display region of the observation image displayed by the aerial display; and a processor programmed to:

detect the at least one of the position and the movement of the object via the detector, and control the drive motor of the optical system in accordance with the detected at least one of the position and the movement of the object in the display region of the observation image displayed by the aerial display.

\* \* \* \* \*